United States Patent [19]

Banko

[11] 4,417,578
[45] Nov. 29, 1983

[54] ULTRASONIC TRANSDUCER WITH ENERGY SHIELDING

[75] Inventor: Anton Banko, The Bronx, N.Y.

[73] Assignee: Surgical Design, Long Island City, N.Y.

[21] Appl. No.: 245,707

[22] Filed: Mar. 20, 1981

[51] Int. Cl.³ .............................................. A61B 17/00
[52] U.S. Cl. .................................. 128/303 R; 604/22; 433/86; 433/119; 310/26
[58] Field of Search ................... 128/303 R, 305, 276, 128/24 A, 328; 433/86, 119; 310/26; 604/22

[56] References Cited

U.S. PATENT DOCUMENTS

| | | | |
|---|---|---|---|
| 3,589,363 | 6/1971 | Banko et al. | 128/303 R X |
| 3,805,787 | 4/1974 | Banko | 128/303 R X |
| 3,809,977 | 5/1974 | Balemuth et al. | 433/119 X |
| 3,896,811 | 7/1975 | Storz | 128/24 A X |
| 4,332,558 | 6/1982 | Lustig | 433/86 |

*Primary Examiner*—Lee S. Cohen
*Attorney, Agent, or Firm*—Darby & Darby

[57] ABSTRACT

An ultrasonic instrument including a stack of laminations for converting electrical energy into mechanical vibratory energy to which is connected at one end an acoustic impedance transformer for converting the vibratory energy into longitudinal movement, with a work tip being connected to the free end of the transformer and a transition region of decreasing cross-sectional area extending between the transformer free end and the work tip. A shield is provided to divert the energy radiated from the transition region away from the work tip.

9 Claims, 3 Drawing Figures

ULTRASONIC TRANSDUCER WITH ENERGY SHIELDING

Various applications exist for an ultrasonic instruments. Some of these include, for example, use in surgical applications such as in dental scalers and compacters, instruments for microsurgery in the eye and other places wherein tissue is to be emulsified, etc.

In general, the ultrasonic instruments of the foregoing type include a stack of laminations to which is attached at one end thereof an acoustic impedance transformer. An elongated work piece is attached to the free end of the acoustic impedance transformer. When electrical energy is applied to the stack of laminations, this is converted into a mechanical motion which acts to vibrate the tip at the end of the work piece.

Vibration of the tip in a media produces mechanical force which is substantially normal to the working surface of the tip. That is, if the end of the tip is flat, then a column type force will be transmitted through a fluid in which the tip is immersed to the object, such as tissue opposite to the vibrating surface.

In general, there is a transition region between the acoustic impedance transformer and the tip 1 of the work piece since the tip, and usually an extending intermediate piece are, of a smaller diameter than the acoustic impedance transformer. This transition region has a curved or stepped surface, with the curved surface being more commonly used. The curved surface of the transition region produces mechanical forces which radiate in many directions, most of which are not in the direction of the main force component from the tip which is to perform the active work. This factor in some measure either detracts from the useful work energy produced by the tip end of the work piece or produces energy which is not totally controllable.

Accordingly, the present invention is directed to an arrangement for controlling the energy produced at the transition region of the work piece. The arrangement includes a shield which is shaped to reflect the mechanical wave energy from the transition region back away from the tip rather than in the direction of the work energy produced by the work piece.

Accordingly, an object of the present invention is to provide an ultrasonic transducer in which the energy from the transition region is controlled.

A further object is to provide a shield for an ultrasonic transducer which reflects energy from the transition region away from the tip.

Another object is to provide a novel acoustic impedance transformer and a shield therefore.

Other objects and advantages of the present invention will become more apparent upon reference to the following specification and annexed drawings in which.

Figure 1:
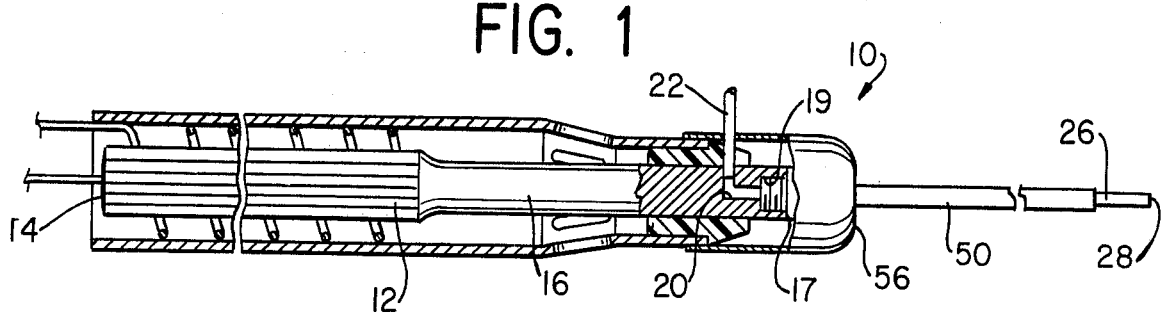
FIG. 1 is a plan view, taken partly in section, of an ultrasonic transducer in accordance with the present invention.

Referring to FIG. 1, the ultrasonic transducer 10 includes a stack of laminations 12 of a suitable material, for example, MONEL. The laminations are connected together at the non-working end 14 and are connected at the other end to one end of an acoustic impedance transformer 16, which can be of stainless steel or other suitable metal. The acoustic impedance transformer is a body of metal of suitable thickness and dimension necessary to convert the vibrations of the laminations 12 into longitudinal motion. The acoustic impedance transformer 16 has an end 17 which is formed with a threaded recess 19. There is a passage 20 from the recess 19 to a fitting 22 external to the transformer 16. A flow line (not shown) can be connected to fitting 22. This particular arrangement is not critical to the invention but it provides a fluid flow passage to the end of the acoustic impedance transformer.

An elongated piece 26 of stainless steel or other suitable metal is provided which has a working tip end 28. The other end of the piece 26 is threaded at 30 to fit into the threaded recess 19 of the acoustic impedance transformer. The piece 26 is hollow along its length and through the threaded stud 30 so that there is a fluid flow passage along the length of the work piece external to the fitting 22.

Figure 2:
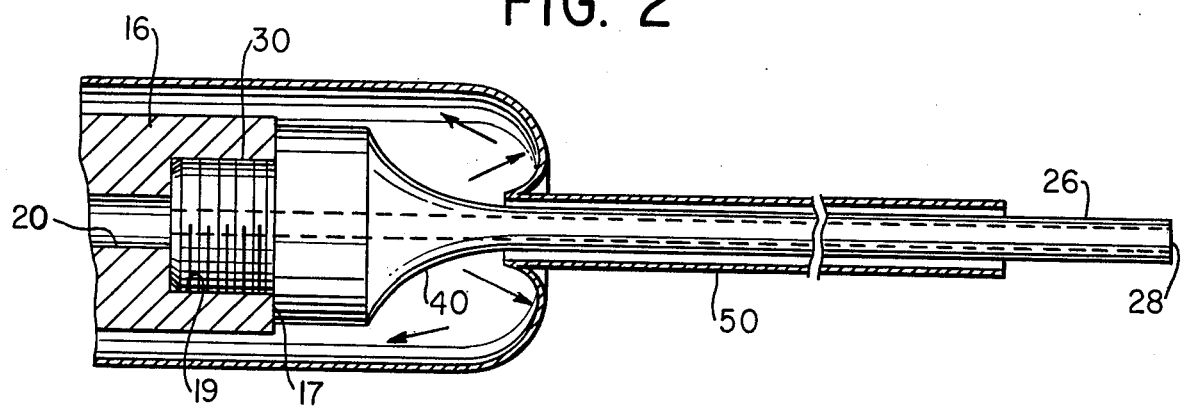
FIG. 2 is an enlarged view in section showing the transition region and the operation of the shield.

As shown in greater enlarged detail in FIG. 2, the work piece has a transition region 40, which is a continuous curved concave surface. The region can have other shapes, for example, a series of stepped cylinders of gradually decreasing diameter with the transition between each of the cylinders being either curved or flat. In some cases, the transducer is constructed so that the transition region is on the acoustic impedance transformer rather than on the work tip. In either case the components are treated as a vibrating structure.

The transducer operates to produce longitudinal movement of the work piece 26. When the tip 28 is immersed in a fluid, a component of force is produced which is normal to the flat surface of the tip. This component of force will move a column of fluid to provide a force on the material being operated upon.

As seen in FIG. 2, at the transition region 40 components of force which will be produced normal to the surface of the region. Thus, there will be components of force in directions away from the desired direction of the main work force component longitudinally along work piece 26 toward tip 28. It is desired that these components from the transition region be kept away from the main body of energy which is being produced by the working end of the tip.

To accomplish this, a shield 50 is utilized. The shield 50 can be of the same material as the tip and/or the acoustic impedance transformer. The shield material is preferably capable of reflecting mechanical energy impinging upon it rather than absorbing this energy. The front of the shield 50 extends substantially along the entire length of the work piece 26 leaving only a small portion of the tip protruding. The rear portion of the shield engages either the acoustic impedance transformer or the housing so that the shield is held to the instrument. The point of engagement is preferably at a nodal point of the vibrating structure. Depending upon the type of engagement, an O-ring seal can be used.

As seen in FIG. 2, the portion of the shield 50 opposing the transition region 40 has a reverse reentrant, i.e. convex, type of bend 56 therearound. The bend is such, as seen by the arrows in FIG. 2, that energy which is radiated from the transition period 40 will hit the shield and will be reflected backward toward the acoustic impedance transformer and the housing. The energy is finally absorbed by the shield and/or transformer and/or housing and is dissipated as heat.

In the prior art, shields were used which had the same overall contour, i.e. concave, as the transition region and extended in the same direction. In such prior art shields, the energy produced from the transition region 40 would impinge upon the shield and would be reflected in a direction toward the elongated part of the work tip. This energy is uncontrolled and would cause a degree of unwanted interference with the tip operation.

Accordingly, the shield 50 of the present invention takes the energy from the transition region of the acoustic impedance transformer and keeps it from impinging upon the working end of the work piece. This prevents the transition region energy from interfering with the operation of such work piece.

Figure 3:
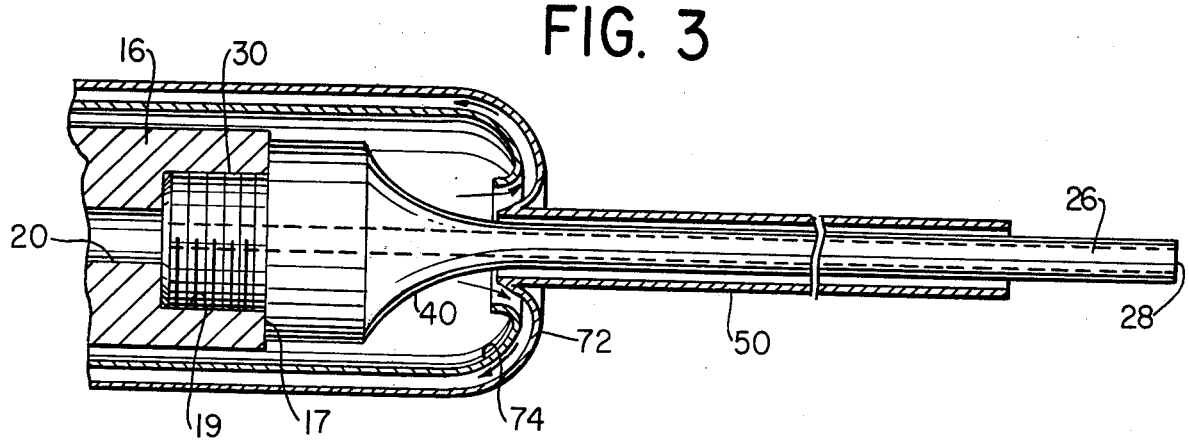
FIG. 3 is an enlarged view of a further embodiment of the invention.

FIG. 3 shows an alternate arrangement for the portion of the shield transition part. In this embodiment, the shield 50 has an inner wall 74 and an outer wall 72 defining a hollow space. The inner and outer walls are connected together in any suitable, conventional manner, for example, by a full or partial connecting wall at the ends closest to the transformer 12, by being inserted into a mounting block, etc. The spacing between the inner and outer walls 74,72 is selected to correspond to the vibrational frequency of the transducer so that the vibrational energy from the transition region will be essentially ducted through the space. Energy which is not directed is reflected as described with respect to FIG. 2.

What is claimed is:

1. In an ultrasonic instrument comprising for converting electrical energy into vibratory mechanical energy, acoustic impedance transformer means connected to said energy converting means and an elongated work piece having a non-linear transition region at one end which is connected to said transformer means and a work tip at the other end, the transformer means and the transition region converting the vibratory energy into longitudinal motion which is transmitted along the work piece to the work tip with there being mechanical energy radiating outwardly from the transition region, and shield means located adjacent and surrounding said transition region and at least a portion of said elongated work piece toward said work tip and spaced away from the entirety thereof, said shield means being generally concentric with said portion of the elongated work piece which it surrounds to form a passage therebetween and having a non-linear region opposing said non-linear transition region for reflecting the mechanical energy radiated from said transition region back toward said converting means and in a direction away from the work piece and the passage between the elongated portion of the work piece and the shield means.

2. An ultrasonic instrument as in claim 1 where the surface of said transition region tapers from a larger cross-sectional area to a smaller cross-sectional area going from said transformer means towards said work tip.

3. An ultrasonic instrument as in claim 2 wherein said transition region has a continuous surface.

4. An ultrasonic instrument as in claim 3 wherein said surface is generally concave.

5. An ultrasonic instrument as in claim 2 wherein the non-linear region of said shield means opposing said transition region is shaped generally opposite to the shape of said transition region.

6. An ultrasonic instrument as in claim 1 wherein the surface of said transition region is curved and generally concave, the non-linear region of said shield means having a reentrant shape in a direction generally opposite the concave surface of the transition region to define an angle of incidence with energy radiated toward the tip end of the work piece such that the angle of reflection of energy incident on said shield means directs the energy back toward said converting means.

7. An ultrasonic instrument as in claim 1 wherein the non-linear region of said shield means has inner and outer walls defining a space therebetween having an opening generally toward said transition region, said non-linear region of said shield means being located relative to said transition region so that at least a part of the radiated mechanical energy enters into said space.

8. An ultrasonic instrument as in claim 7 wherein the surface of said transition region is generally concave, said inner and outer walls of said shield means shaped to define the space therebetween to be also generally concave in a direction opposite to that of said surface of said transition region.

9. An ultrasonic instrument as in claim 1 wherein said transition region tapers from a larger cross-sectional area to a smaller cross-sectional area in a direction going from said energy converting means toward said tip end of said work piece, said non-linear region of said shield means having a reentrant shape defining an angle of incidence with the energy radiated from said transition region toward said tip end such that the angle of reflection of energy incident on said shield means in the area adjacent said transition region is back toward said converting means.

* * * * *